United States Patent [19]

Balázs et al.

[11] 4,384,991
[45] May 24, 1983

[54] PROCESS FOR THE PREPARATION OF A BIOLOGICALLY ACTIVE SUBSTANCE FOR SELECTIVE INHIBITION OF THE PROLIFERATION OF LEUKEMIC AND NORMAL MYELOID CELLS

[75] Inventors: András Balázs; Mihály Sajgó; Lajos Kisfaludy; Tibor Klupp; Kornélia Barabás née Borbás, all of Budapest, Hungary

[73] Assignee: Richter Gedeon Vegyeszeti Gyár Rt., Budapest, Hungary

[21] Appl. No.: 223,366

[22] Filed: Jan. 8, 1981

[30] Foreign Application Priority Data

Jan. 15, 1980 [HU] Hungary ................................. 68/80

[51] Int. Cl.$^3$ .............................................. C07G 7/00
[52] U.S. Cl. ............................ 260/112 B; 260/112 R; 424/101
[58] Field of Search ...................... 260/112 R, 112 B; 424/101

[56] References Cited

U.S. PATENT DOCUMENTS 4,294,824 10/1981 Jones ................................. 424/101

OTHER PUBLICATIONS

Chem. Abst.: 86:39580q, 90:163664s, 93:24173e, 93:63891g.
Paukovits, W. R. Chem. Abs. 85:189853z.
Rytomaa, T. Chem. Abs. 81:73662z.

*Primary Examiner*—Allan Lieberman
*Assistant Examiner*—Patricia Short
*Attorney, Agent, or Firm*—Karl F. Ross; Herbert Dubno

[57] ABSTRACT

The invention relates to a process for the preparation of a biologically active substance, which can be isolated from normal white blood cells and is capable of inhibiting the proliferation of normal and leukemic myeloid cells selectively.

The substance obtained is a peptide, which has an amino acid composition of $Tau_1$, $Asx_1$, $Ser_2$, $Thr_1$, $Glx_3$, $Gly_2$, $Ala_1$, $(PO_4)_1{}^{2-}$, a negative charge at pH 6.5, an electrophoretic mobility of $-0.55$ to $-0.65$ related to aspartic acid, has no charge at pH 1.9, has a mobility of about 0.26 related to $\epsilon$-DNP-lysine and gives a positive chloro-toluidine reaction.

11 Claims, No Drawings

PROCESS FOR THE PREPARATION OF A BIOLOGICALLY ACTIVE SUBSTANCE FOR SELECTIVE INHIBITION OF THE PROLIFERATION OF LEUKEMIC AND NORMAL MYELOID CELLS

This invention relates to a process for the isolation of a biologically active substance from normal white blood cells. The substance is capable of inhibiting the proliferation of normal and leukemic myeloid cells selectively.

It is well known that the cytostatic substances used in the chemotherapy of malignant tumors, such as alkylating agents, anti-metabolites and spindle poisons, generally are highly toxic compounds which injure all kinds of fissiparous cells. Since melignant tumors are pathological forms of a given type of cell, it is desirable to employ selective substances for inhibiting the proliferation of these cells [S. Eckhardt: Klinikai Onkologia, Medicina, Budapest, 1977].

As a result of extensive research activity, up to the present time the preparation of about 25 cell extracts prepared from various uniform cell tissues, which contain naturally occurring regulators for the selective inhibition of the proliferation of specific types of cells, has been reported [A. Balázs, I. Blazsek: Control of Cell Proliferation by Endogenous Inhibitors, Akademiai Könyvkiadó, Budapest and Elsevier—North Holland, 1979]. Especially favorable results were obtained by the purified extracts of white blood cells (granulocytes) [Rytömaa and Kiviniemi: Cell Tissue Kinet. 1, 341 (1968); Paukovits: Nat. Cancer. Inst. Monogr. 38, 147; Paukovits et al: Oncology 34, 187 (1977)]. The biological activity of the partially purified granulocyte extract has been demonstrated also on leukemic patients [Rytömaa et al, Scand. J. Haematol., Suppl. 27, 5 (1976)]. In the Hungarian patent specification No. 162,446 a process is disclosed for the preparation of a partially purified granulocyte extract from human and calf blood or peritoneal liquid. The extract obtained inhibits the proliferation of white blood cells selectively.

The various extracts reported hereinbefore are, however, only partially purified preparation, which contain a substantial amount of impurities. There is no method known in the art for the preparation of pure biologically active substances which are capable of selective inhibition of the proliferation of specific cells.

It has now been found that by a further development of the methods disclosed in our Hungarian patent specification No. 162,446 the problem of preparing such a pure active substance can be solved. More particularly, it has been found that by subjecting suitable starting materials, preferably extracts of white blood cells isolated from horse blood or calf spleen to specific fractionating operations, a chemically pure, uniform, well characterizable oligopeptide-like active substance can be obtained, which inhibits the proliferation of leukemic myeloid cells even in extremely low concentrations.

The invention relates to a process for the preparation of a biologically active substance, which can be isolated from normal white blood cells and is capable of inhibiting the proliferation of normal and leukemic myeloid cells selectively, characterized by (a) homogenizing white blood cells isolated from animal or human blood, preferably from horse blood in a buffer solution having a pH of 7 to 8, centrifuging the liquid homogenizate, separating the dissolved fraction having a molecular weight of less than 10,000 from the supernatant liquid, subjecting this fraction to a further fractionation, preferably by chromatography, isolating and if desired, lyophilizing the fraction obtained at a volume of $v_e/v_o = 1.15$ to $1.45$ (the active and specific fraction can be traced between the elution maximum of $^3$H-thymidine used as a marker and $v_o$); or (b) homogenizing animal organs containing granulocytes, especially calf spleen in a water-miscible organic solvent, separating the solid substances from the liquid suspension obtained, extracting them with an organic solvent capable of dissolving fats, extracting the solid residue with water, separating the undissolved fraction, isolating from the liquid phase left behind the dissolved components having a molecular weight of less than 10,000, subjecting this fraction to a further fractionation, preferably by gel chromatography, and separating and if desired, lyophilizing the fraction obtained at a volume of $v_e/v_o = 1.3$ to $2.5$ (the active and specific fraction can be detected between the elution maximum of $^3$H-thymidine used as a marker and $v_o$), and purifying the product prepared by process variant (a) or (b) by ion exchange chromatography, fractionating on the basis of ion charge and size (for example by column chromatography, carried out on a Dowex 50×8 chromatographic column) or by paper electrophoresis, and isolating a peptide, which has a negative charge at pH 6.5, a relative mobility of $-0.55$ to $-0.65$ related to aspartic acid; has no charge at pH 1.9; has a mobility of 0.26 related to $\epsilon$-DNP-lysine; does not have a free amino group; and according to amino acid analysis has the following composition: $Tau_1$, $Asx_1$, $Ser_2$, $Thr_1$, $Glx_3$, $Gly_2$, $Ala_1$, $(PO_4)_1{}^{2-}$.

The fraction directly obtained by process variant (a) or process variant (b) is referred to below as "fraction GI-3", The end product may also be designated by "GP", for short, which stands for "granulopeptide".

The GP substance according to the invention has a selective activity. It specifically inhibits the proliferation of myeloid cells (granuloid cells of mice and rats, transplantable animal myeloid leukemic cells, spontanous human acute myeloid leukemic cells), and is ineffective against normal thymocytes, PHA-stimulated lymphocites, subacute lymphoid leukemic thymocytes, human lymphoid leukemic blood cells and HeLa human tumor cells.

The fraction GI-3 obtained as an intermediate fraction in the process according to the invention naturally also contains the GP active substance, accompanied by less active components and a large amount of inactive impurities. The GI-3 fraction also shows a specific inhibiting activity against the proliferation of myeloid cells, to an extent corresponding to its GP active ingredient content. In in vitro experiments the minimum effective dose (MED) of the GI-3 fraction when inhibiting the incorporation of $^3$-H-thymidine into acid-insoluble DNS amounts to 110 $\mu$g/ml., while in the case of capillary colonies formed in agar gel the MED is 8 $\mu$g/ml. The corresponding $ED_{50}$-values are 430 and 90 $\mu$g/ml., respectively.

The physico-chemical and cell biological characteristics of the active substance prepared according to the invention are as follows:

Duration of effect
    in suspension cultures: >8 hours
    in gel colonies: 1 week.

The active substance is not toxic since it does not reduce cell vitality as measured by $^{51}$Cr-release test. Its point of attack is the $G_1$ phase of the cell cycle. Thrmostability:

The substance does not lose its activity and the specific character of its activity after a treatment at 80° C. for 60 minutes; in solution in a period of 72 hours no decrease in activity can be observed. The substance can be stored as a lyophilizate at −20° C. for more than 7 weeks, in the form of acetone- or chloroform-powder at +4° C. for more than 18 months.

The results of in vitro tests carried out to compare the activity of the GP active substance isolated by ion exchange chromatography or paper electrophoresis and retested with the activity of the GI-3 fraction and the pure GP active substance are shown in the Tables I and II below.

TABLE I

The effect of 100 μg/ml. GP on the incorporation of $^3$H—thymidine into acid-insoluble DNS in bone marrow and thymus cell cultures

| Number of experiments | Bone marrow inhibition in % of the control | P | Thymus inhibition in % of the control | P |
|---|---|---|---|---|
| 12 | 53.2 | <0.001 | 14.6 | <0.2 |
| 14 | 59.9 | | 7.3 | |

TABLE II

The dose-effect relation of the GI-3 fraction and GP isolated therefrom

| Test | GI-3 fraction μg/ml. MED | GI-3 fraction μg/ml. ED$_{50}$ | Granulopeptide (GP) pmoles/ml. MED | Granulopeptide (GP) pmoles/ml. ED$_{50}$ |
|---|---|---|---|---|
| Incorporation of $^3$H—thymidine into bone marrow, suspension cultures, 3-4 hours | 100 * | 430 * | 2.5 * | 7.8 * |
| Formation of colonies in an agar gel capillary, 7 days | 8 * | 90 * | 0.2 ** | 1.6 ** |

* = measured values
** = calculated values

The active compound GP prepared according to the invention can be used for the inhibition of proliferation of normal and leukemic human bone marrow and blood cells in vitro in a concentration of 0.2 to 10.0 picomole/ml.

Further details of the invention are to be found in the following nonlimiting Examples.

EXAMPLE 1

The preparation of GI-3 fraction from horse blood 10 l. of horse blood are treated with 3500 E/l. heparin. The blood then sedimentated at room temperature for 30 minutes, whereupon the upper layer rich in leukocytes in separated and centrifuged at 800 g. The cell population separated, which contains 80% of granulocytes is washed in 200 ml. of a 0.06 M phosphate buffer solution (pH=7.4) under centrifuging at 800 g. The composition of the phosphate buffer is: 9.500 g. of disodium hydrophosphate. 2H$_2$O and 1.815 g. of potassium dihydrophosphate in 1 l. of distilled water. The granulocyte precipitate obtained is suspended in a phosphate buffer having the above composition, in a density of 4.10$^9$ cells/ml., in a Potter homogenizor, by 10 pulls per minute.

The homogenizate obtained is centrifuged for 30 minutes at 1500 g. The separated supernatant liquid is subjected to ultra filtration using an Amicon PM 10 membrane, under a pressure of 3 atm. The filtrate obtained is lyophilized and the lyophilizate obtained is subjected to gel chromatography on a Sephadex G-10 column, using a 0.05 M ammonium hydrogencarbonate buffer solution (pH=7.9). The fraction corresponding to $v_e/v_o=1,15$ to 1.45 is separated und lyophilized. Thus 65 mg. of a solid active substance concentrate (fraction GI-3) are obtained.

EXAMPLE 2

Preparation of fraction GI-3 from calf spleen

To 1000 g. of chopped calf spleen, released from its fibrous layer, acetone at 4° C. is added up to 4 l. The mixture is homogenized at this temperature, incubated for 60 minutes, centrifuged and the separated precipitate is washed with acetone and dried at 20° C. in vacuo.

The dry substance is extracted for 30 minutes with 2 lit. of chloroform, the solid phase is separated, dried at room temperature and dissolved in 3 l. of twice-distilled water with stirring for 16 hours. The solution is centrifuged at 20,000 g. for 1 hour. The supernatant liquid phase is filtered through Amicon XM 50 and thereafter on a PM 10 membrane under a pressure of 3 atm. The filtrate is lyophilized. The lyophilizate obtained is subjected to gel chromatography on a Sephadex G-15 column using a 0.05 M ammonium hydrogencarbonate buffer solution (pH=7.9). The fraction corresponding to $v_e/v_o=1.3$ to 2.5 is separated and lyophilized. Thus 3.54 g. of a solid active ingredient concentrate (fraction GI-3) are obtained.

EXAMPLE 3

Preparation of pure GP active substance 300 mg. of an active ingredient concentrate GI-3 prepared according to Example 1 or Example 2 are applied to a Whatman 3 MM chromatographic paper starting from the middle of the paper, in a length of 30 cm. Electrophoresis is carried out in a 90:4:900 mixture of pyridine, acetic acid and water (buffer, pH=6.5), in a horizontal apparatus, with a voltage gradient of 50 V/cm, for 2 hours. The position of the acidic ninhydrine-negative and chlorine-positive component is determined by dying with chloro-toluidine. The active component obtained is eluted from the paper by a 8:2:90 mixture of acetic acid, formic acid and water and is subjected to a further electrophoresis in this buffer mixture (pH=1.9) at 80 V/cm, for 90 minutes. The position of the uncharged component (GP active substance) is determined by a chloro-toluidine reaction. The substance obtained is eluted from the paper by the acidic buffer mixture described above and the eluate is lyophilized. Thus 8 μg. of pure GP substance are obtained.

What is claimed is:

1. A process for the preparation of a biologically active substance inhibiting the proliferation of normal and leukemic myeloid cells selectively, from an extract of normal white blood cells, which comprises the steps of:
   (a) homogenizing white blood cells isolated from animal or human blood in a buffer solution having a pH of 7 or 8, centrifuging the liquid homogenizate, separating the dissolved components having a molecular weight of less than 10,000 from the supernatant liquid, subjecting this fraction to a further fractionation by chromatography on Sephadex G 10 or a material similar thereto, and isolating the fraction obtained between $v_e/v_o=1.15$ and 1.45; or (b) homogenizing animal organs containing granulocytes, preferably calf spleen, in a water-miscible organic solvent, separating the solid substances from the liquid suspension obtained, extracting them with an organic solvent capable of dissolving fats, extracting the solid residue with water, separating the undissolved fraction, separating from the liquid phase the dissolved components having a molecular weight of less than 10,000, subjecting this fraction to a further fractionation by chromatography on Sephadex G 15 or a material similar thereto, and separating the fraction obtained between $v_e/v_o = 1.3$ and 2.5; and (c) purifying the product prepared by step (a) or (b) by paper electrophoresis, and isolating the peptide, which has a negative charge at pH 6.5, a relative mobility of $-0.55$ to $-0.65$ related to aspartic acid, has no charge at pH 1.9, has a mobility of about 0.26 related to $\epsilon$-DNP-lysine, and gives a positive chloro-toluidine reaction.

2. The process defined in claim 1 wherein said blood in step (a) is horse blood.

3. The process defined in claim 1 or claim 2 wherein the components in step (a) or step (b) having a molecular weight less than 10,000 are separated by molecular filtration.

4. The process defined in claim 1 or claim 2 wherein acetone is said water-miscible organic solvent.

5. The process defined in claim 1 or claim 2 wherein the solid substances are separated from the suspension in step (b) by centrifuging.

6. The process defined in claim 1 or claim 2 wherein said organic solvent capable of dissolving fats is a chlorinated hydrocarbon.

7. The process defined in claim 1 or claim 2 wherein the fraction isolated in step (a) is subjected to lyophilization.

8. The process defined in claim 1 or claim 2 wherein the fraction obtained in step (b) is subjected to lyophilization.

9. The process defined in claim 1 or claim 2 wherein the isolated peptide is subjected to lyophilization.

10. The peptide made by the process of claim 2.

11. The peptide capable of inhibiting the proliferation of normal and leukemic myeloid cells selectively made by the process defined in claim 12 and having an amino acid composition of $Tau_1$, $Asx_1$, $Ser_2$, $Thr_1$, $Glx_3$, $Gly_2$, $Ala_1, (PO_4)_1{}^{2-}$, a negative charge at pH 6.5 an electrophoretic mobility of $-0.55$ to $-0.65$ related to aspartic acid, having no charge at pH 1.9, having a mobility of about 0.26 related to $\epsilon$-DNP-lysine and giving a positive chloro-toluidine reaction.

* * * * *